United States Patent [19]

Terni et al.

[11] Patent Number: 4,923,859
[45] Date of Patent: May 8, 1990

[54] PYRIDO-BENZOTHIAZINE DERIVATIVES HAVING HIGH ANTIBACTERIAL ACTIVITY AND HIGH BIOAVAILABILITY TO TISSUES

[75] Inventors: Patrizia Terni; Stefano Maiorana; Antonio Papagni; Piergiuseppe Pagella, all of Milan, Italy

[73] Assignee: Mediolanum farmaceutici, S.r.l., Italy

[21] Appl. No.: 251,457

[22] Filed: Sep. 30, 1988

[30] Foreign Application Priority Data

Oct. 6, 1987 [IT] Italy ............................ 22156 A/87

[51] Int. Cl.$^5$ .................... A61K 31/54; C07D 513/06
[52] U.S. Cl. ................................. 514/224.5; 544/32
[58] Field of Search ................... 544/32; 514/224.5

[56] References Cited

U.S. PATENT DOCUMENTS 4,571,396 2/1986 Hutt et al. ............. 514/224.5 X
4,684,647 8/1987 Mascellani et al. .......... 544/32 X

FOREIGN PATENT DOCUMENTS 267432 5/1988 European Pat. Off.
203085 12/1982 Japan.

OTHER PUBLICATIONS

Daüchi Seiyaku Co. Chemical Abstracts, vol. 98(1983) 198294p.
Otsuka Pharm. Co., Chemical Abstracts, vol. 101(1984) 151868u.
Cecchetti et al., Chemical Abstracts, vol. 106(1987) 102235e.
Terni et al., Chemical Abstracts, vol. 109(1988) 129034.

*Primary Examiner*—Richard L. Raymond
*Attorney, Agent, or Firm*—Arnold, White & Durkee

[57] ABSTRACT

Pyrido-benzothiazine derivatives having the following general formula:

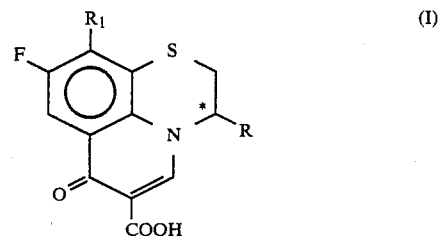

in which R is H or a $C_1$–$C_6$ alkyl or a $C_1$–$C_6$ fluoroalkyl, and $R_1$ is N-alkyl-3-pyrrolidinalkylamine with $C_1$ to $C_6$ alkyls or

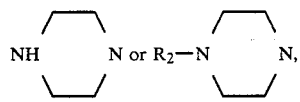

where $R_2$ is a $S_1$–$C_6$ alkyl or a $C_2$–$C_6$ alkenyl or an arylalkyl group, possibly substituted by halogen, hydroxy or keto-groups, both in the racemic form and in the optically active form.

The invention also comprises the process for the preparation of derivatives of formula (I) starting from 2.4-difluoro-3-chloronitrobenzene.

Said derivatives possess a high antibacterial acitvity as well as a high bioavailability to tissues; the invention also refers to pharmaceutical compositions containing them as active components.

2 Claims, No Drawings

PYRIDO-BENZOTHIAZINE DERIVATIVES HAVING HIGH ANTIBACTERIAL ACTIVITY AND HIGH BIOAVAILABILITY TO TISSUES

FIELD OF THE INVENTION

The invention refers to new pyrido-benzothiazine derivatives having high antibacterial activity as well as high bio-availability to tissues, to a process for their preparation, and to pharmaceutical compositions containing them as active principles.

PRIOR ART

Pyrido benzothiazine derivatives of quinolone type, possessing antibacterial activity are described in Jpn Kokai 57-203085 and Jpn Kokai 59-76091 patents. A wide series of amino-substituted quinolones excluding pyrido-benzothiazine derivatives, such as for instance N-alkyl-3-pyrrolidinmethanamines, are described in the E.P. 0106489.

Recently, fluorinated (fluoroalkyls) substituents in position 3 of pyrido-benzoxazine were claimed in Jpn Kokai 61,204,188 and Jpn Kokai 61,271,292 patents.

Pyridobenzothiazine structures are further known, having wide and powerful antibacterial activity as well as favorable pharmacokinetic characteristics, such as a high bio-availability to tissues and a long half-life as described in the Italian Patent Applications 19790 A/84, 19812 A/85, 21999 A/86 and as illustrated by A. Fravolini, P. Terni, G. Mascellani, P. G. Pagella, G. Segre, "Pharmacokinetics of a new Quinolone of the Pyrido-benzothiazine Series". Recent Advances in Chemotherapy, Ed. by J. Ishigami, 1985, 640–641, and by V. Cecchetti, A. Fravolini, R. Fringuelli, G. Mascellani, P. G. Pagella, M. Palmioli, G. Segre, P. Terni, Quinolonecarboxylic Acids. 2. Synthesis and Antibacterial Evaluation of 7-oxo-2,3-dihydro-7H-pyrido [1,2,3-de][1,4]benzothiazine-6-carboxylic Acids, J. Med. Chem. 1987, 30, 465–473.

SUMMARY OF THE INVENTION

We have now found a new series of pyrido-benzothiazine derivatives of quinolone type having powerful antibacterial activity and high bio-availability.

Said derivatives have the following general formula

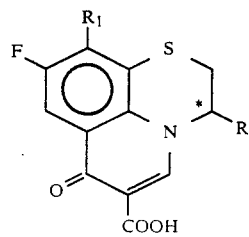

(I)

in which R=H, $C_1$-$C_6$ alkyl, $C_1$-$C_6$ fluoroalkyl, $R_1$=N-alkyl-3-pyrrolidine-alkylamine with $C_1$-$C_6$ alkyls, or

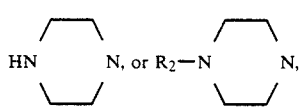

wherein $R_2$ is a $C_1$-$C_6$ alkyl or a $C_2$-$C_6$ alkenyl or an arylalkyl-group, possibly substituted by halogen, hydroxy or keto-groups.

R is preferably a $C_1$-$C_6$ alkyl or fluoroalkyl and the N-alkyl-3-pyrrolidine-alkylamine is preferably a N-alkyl-3-pyrrolidinmethanamine.

Enclosed table 1 shows that, differently from what previously observed in similar structures (I. Hayakawa et al. in Recent advances in chemoterapy, Ed. by J. Ishigami 1985, WS-9-3), the sulphur atom imparts to the structures claimed in the present invention an antibacterial activity equal to or higher than the oxygen atom.

The compounds of formula (I) are prepared as follows:

a first reaction cycle in which, starting from 2,4-difluoro-3-chloro-nitrobenzene, the intermediate

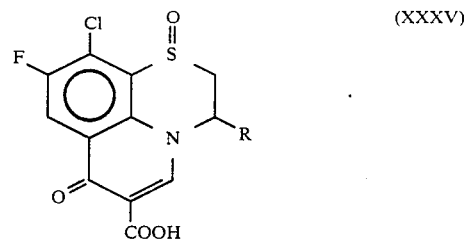

is prepared, and a second reaction cycle in which the nucleophilic substitution of chlorine atom in (XXXV) with a N-alkyl-3-pyrrolidine alkylamine or with

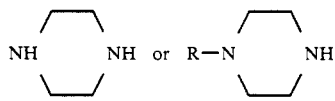

is performed the sulfoxide group is then reduced to sulphide.

Since the products of formula (I) contain an asymmetrical carbon atom (indicated by an asterisk), it is possible to prepare the relevant optically active isomers by resolution of the racemic mixtures.

The optically active compounds obtainable by resolution of the racemic mixtures are intended to be included in the present invention and protected by the same.

In relation to the powerful antibacterial activity and high bio-availability of the pyrido-benzothiazine derivatives of general formula (I), the present invention also refers to the pharmaceutical compositions containing them.

DETAILED DESCRIPTION OF THE INVENTION

The intermediate compound (XXXV), in which R=H is prepared according to a known technique (Italian Patent Application 19790 A/84). The intermediate (XXXV) in which R=$CH_3$, indicated as compound (X), is prepared according to the following reaction cycle:

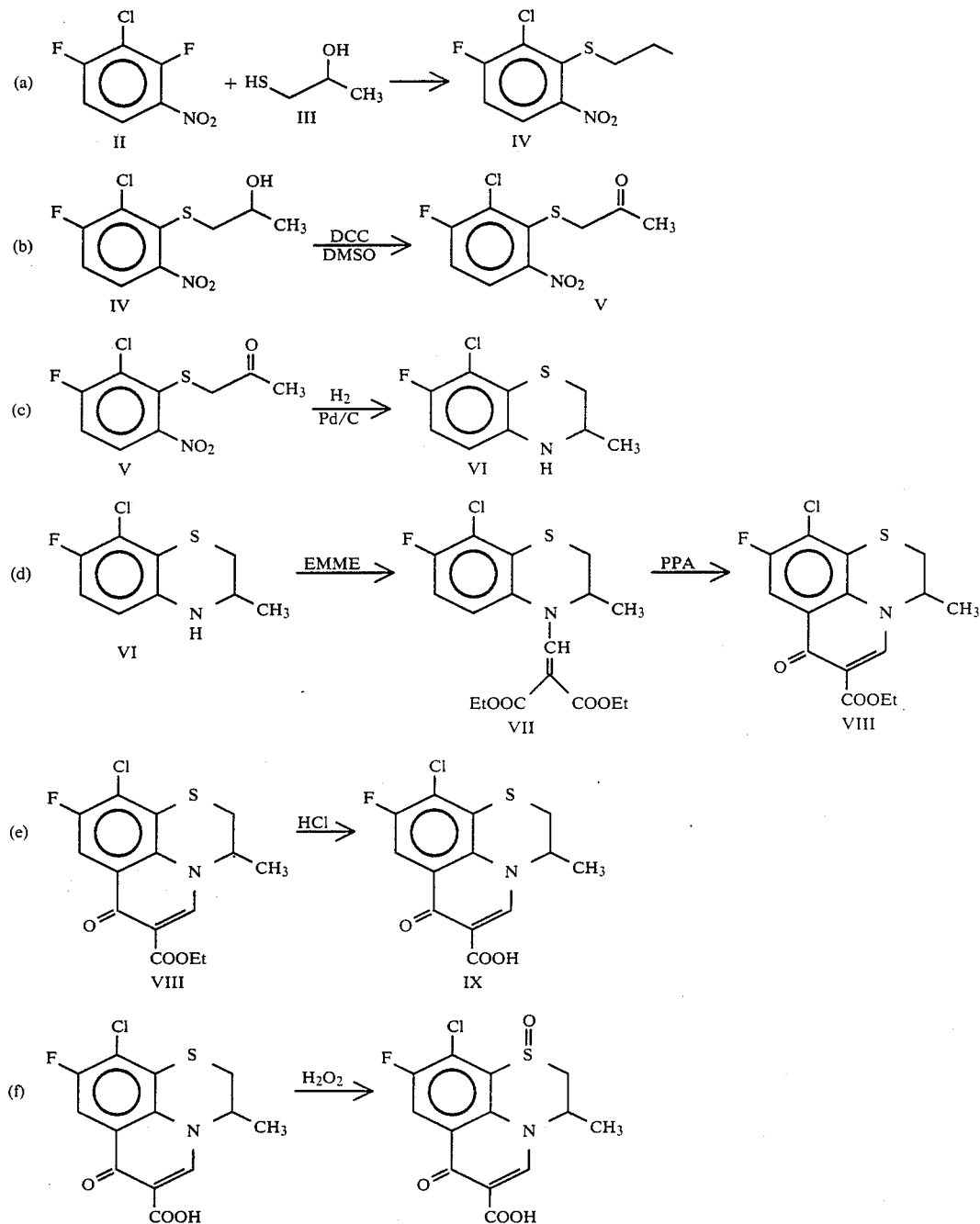

Reaction (a) is carried out using as a solvent dimethoxyethane in the presence of triethylamine, at a temperature between −12° and −8° C. during the mixing of the reagents and at room temperature thereafter.

Reaction (b) is carried out by dissolving product (IV) and dicyclohexylcarbodiimide (DCC) in ethyl ether, adding DMSO and pyridine and then, at 0° C., trifluoroacetic acid.

Reaction (c) is carried out by dissolving product (V) in methanol, adding Pd 10% on carbon and hydrogenating at 90°–110° C. and 40–60 atm, crude product (VI) is purified through the formation of p-toluensulphonate.

Reaction (d) is carried out by heating at 150°–170° C. under stirring a mixture of (VI) with diethylethoxymethylenmalonate (EMME), distilling the alcohol which is formed and treating the resulting product (VII) with polyphosphonic acid (PPA) at 150°–170° C.

Reaction (e) is carried out by treating compound (VIII) with concentrated HCl mixed with water in a ½ volume ratio and heating under reflux.

Reaction (f) is carried out by suspending product (IX) in formic acid, adding 30% $H_2O_2$ and stirring for 40 minutes.

Compound (X) is thus obtained which corresponds to general formula (XXXV) in which R=$CH_3$.

For preparing the compound of general formula (XXXV) in which R=$CH_2F$, indicated as compound (XXXII), one goes through the following reaction cycle.

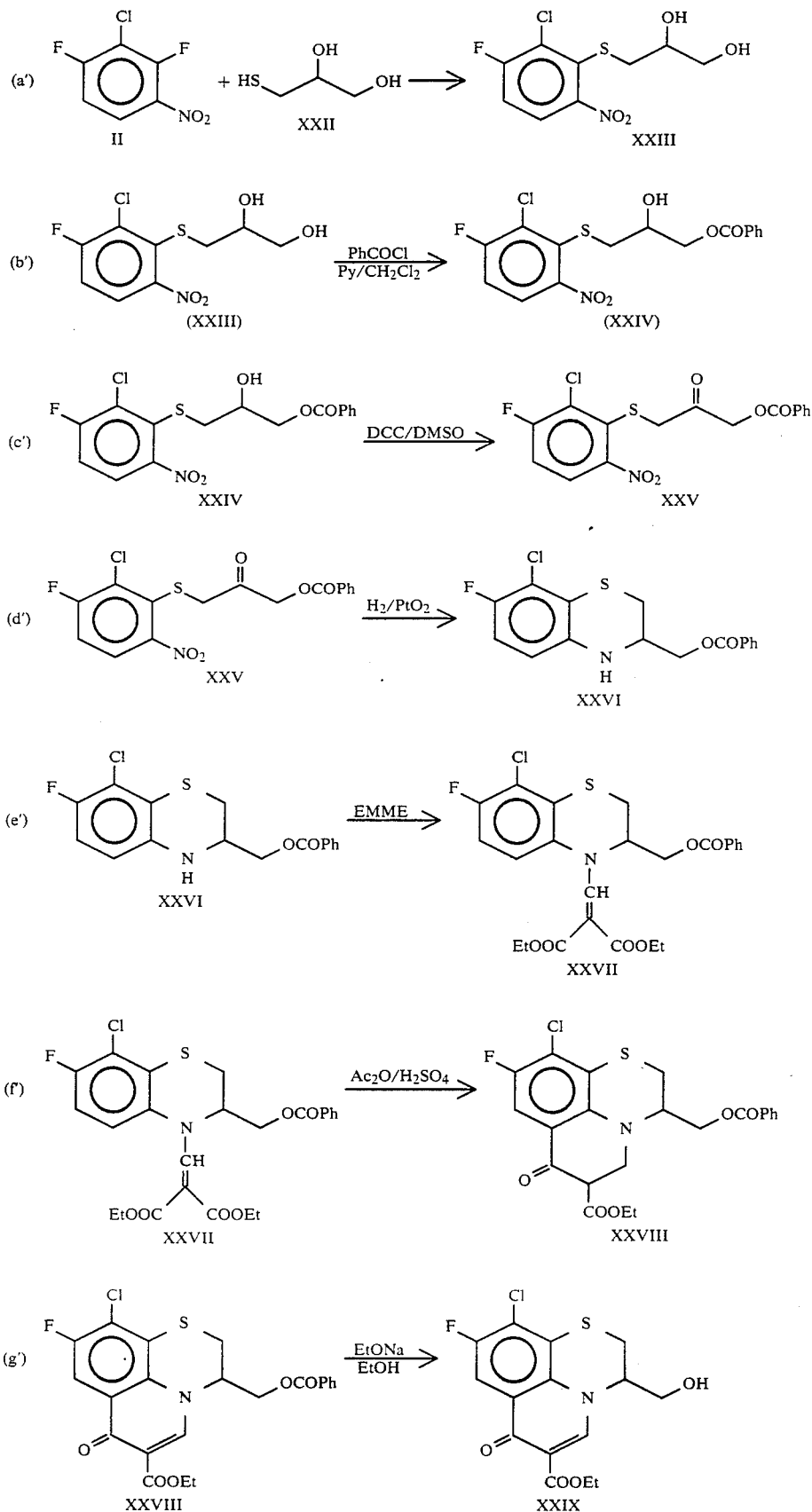

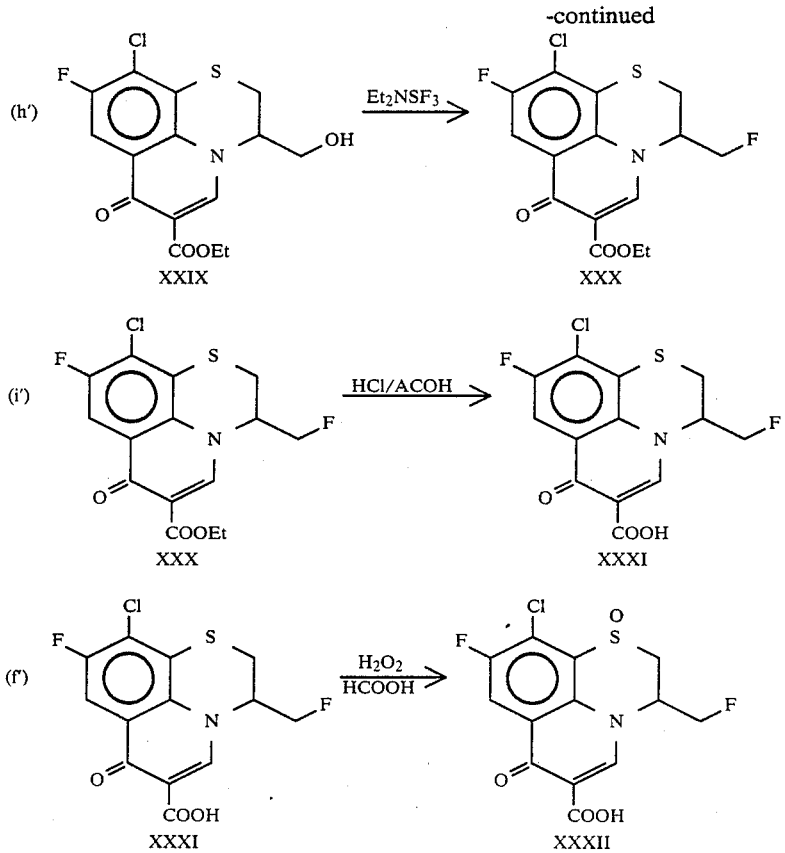

Reaction (a') is carried out adding, at a temperature between −8° and −12° C., compound (XXII) dissolved in dimethoxyethane to a mixture of compound (II) and triethylamine dissolved in dimethoxyethane and bringing then to room temperature.

For reaction (b') benzoyl chloride dissolved in $CH_2Cl_2$ is slowly added to a solution of (XXIII) in methylene chloride-pyridine.

Reaction (c'), oxydation of (XXIV), is carried out at 0° C. with dicyclohexylcarbodiimide and dimethylsulfoxide in diethyl ether.

For reaction (d') compound (XXV) is hydrogenated at normal pressure and room temperature using $PtO_2$ as catalyst.

Reaction (e') is carried out by heating at 150°–170° C. under stirring a mixture of (XXVI) with diethylethoxymethylenmalonate (EMME) and distilling off the ethanol which is gradually formed.

For reaction (f') a mixture of compound (XXVII) and sulphuric acid in acetic anhydride is heated at 70° C. for 40 minutes.

Reaction (g'), hydrolysis of benzoic ester (XXVIII), is carried out in ethanol with 2 equivalents of sodium ethylate.

In reaction (h') a large excess of diethylaminosulphotrifluoride is added at room temperature to a suspension of (XXIX) in $CH_2Cl_2$.

Hydrolysis reaction (i') is carried out by heating under reflux for about 3 hours compound (XXX) in a mixture of HCl and AcOH.

For reaction (l') compound (XXXI) is reacted at room temperature with performic acid, prepared by mixing formic acid and 30% $H_2O_2$.

Thus, compound (XXXII) is obtained corresponding to general formula (XXXV) wherein R=$CH_2F$.

The preparation of compounds of general formula (I) from the intermediates of general formula (XXXV) is performed by means of the following two reactions:

nucleophilic substitution of chlorine atom in (XXXV) by reaction with a N-alkyl-3-pyrrolidinealkylamine or with

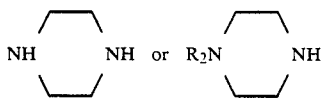

in DMF at 60°–80° C.;

reduction of the sulphoxide group to sulphur group by treatment with $PCl_3$ in DMF or with other reducing agents such as sulfite, bisulfite, metabisulfite.

Since the products of formula (I) contain an asymmetrical carbon atom (indicated by an asterisk), the relevant optically active isomers are prepared by resolution of the racemic mixtures.

The following examples of preparation are reported to illustrate the process of the present invention.

EXAMPLE 1

Preparation of:

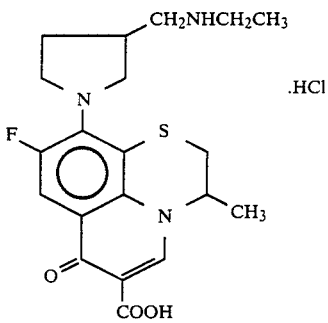

10[3-[(ethylamino)methyl]-1-pyrrolidinyl]9-fluoro-2,3-dihydro-3-hydrochloride 11 g (0.041 mols) nitroalcohol (IV) and 16.9 g (0.082 mols) dicyclohexylcarbodiimide (DCC) are dissolved in 160 ml ethyl ether and added with 3.7 ml (0.0521 mols) DMSO and 0.6 ml (0.0074 mols) pyridine; to the solution thus obtained cooled to 0° C., 0.6 ml (0.0078 mols) trifluoroacetic acid are added dropwise.

The temperature is allowed to rise to room value and the mixture is kept under stirring for 40'.

3.87 g (0.043 mols) oxalic acid are then added until the $CO_2$ development stops, in order to eliminate the excess of dicyclohexylcarbodiimide, the product is diluted with ethyl ether and the dicyclohexylurea formed is filtered off, a saturated solution of sodium bicarbonate is added, after drying and evaporation of the organic layer the residue, taken up with the smallest amount of isopropyl ether, gives 7.96 g of acetonyl-thio-3-chloro-4-fluoro nitrobenzene as a white solid. Yield 72.9%. m.p. 91°-92° C.

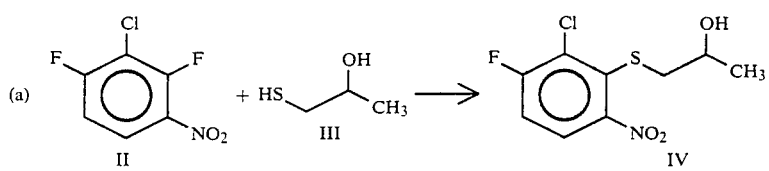

17.8 g (0.092 mols) 2,4-difluoro-3-chloro-nitrobenzene are dissolved in 170 ml dimethoxyethane, 15.6 ml (0.112 mols) of triethylamine are added and the mixture is cooled to $-10°$ C. While keeping this temperature, 10 g (0.109 mols) of 1-mercapto-2-propanol are added dropwise; the temperature is then allowed to rise up to room and stirring is continued overnights.

The mixture is poured into water and the product is reapetedly extracted with $CHCl_3$; the combined organic extracts are dried on sodium sulphate and the solvent is removed under reduced pressure. The residue is subjected to chromatography on silica gel using as eluent a 1/1 petroleum ether/diethyl ether mixture; the head fractions are collected which give 13.7 g of 3-chloro-4-fluoro-2-(2-hydroxypropyl-1-thio) nitrobenzene as a yellow oil.

Yield 56%. IR (film) 3.390 cm$^{-1}$ ($\nu$O—H).

$^1$H—NMR (CDCl$_3$—TMS) $\delta$1.26 (3H,d,—CH$_3$)2.9(1H,s,O—H)3.16-3.51(2H,-m,—S—C$\underline{H}_2$)

3.92(1H.m.C$\underline{H}$—)

7.35(1H,m,C$_5$—$\underline{H}$)7.62(1H,m,C$_6$—$\underline{H}$).

IR(nujol) 1.700 cm$^{-1}$ ($\nu$c=o).

$^1$H—NMR (CDCl$_3$—TMS) $\delta$ 2.31(3H,s,COCH$_3$) 3.81(2H,s,—SCH$_2$COCH$_3$) 7.12(1H,m,C$_5$—$\underline{H}$) 7.59(1H,m,C$_6$—$\underline{H}$).

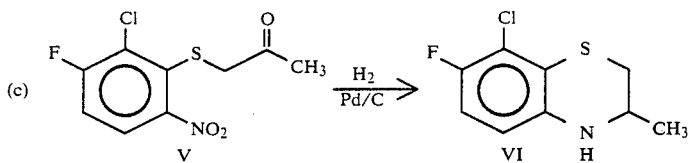

To 4.3 g (0.016 mols) of ketone (V) dissolved in 200 ml methanol, 1 g Pd 10% on carbon is added; the mixture obtained is hydrogenated under 50 atm pressure at 100° C. for 20 hrs. The catalyst is then eliminated by filtration on a celite bed and the remaining solution, after removing the solvent under reduced pressure, gives a brown oil consisting of raw 8-chloro-7-fluoro-3-methyl-2,3-dihydro-4H-1,4-benzothiazine which is purified through formation of the p-toluensulphonate.

The oil is dissolved in dienyl ether and a saturated ether solution of p-toluensulphonic acid is added to acidic pH; a whitish solid precipitates which is filtered and washed with ethyl acetate.

The solid is then suspended in a water-isopropyl ether mixture and a saturated sodium bicarbonate solution is added until basic pH.

The ether phase containing the purified benzothiazine is dried and evaporated, obtaining 1.4 g of yellow oil. Yield 39.4%.

I.R. (film) 3.400 cm$^{-1}$ ($\nu$N—H).

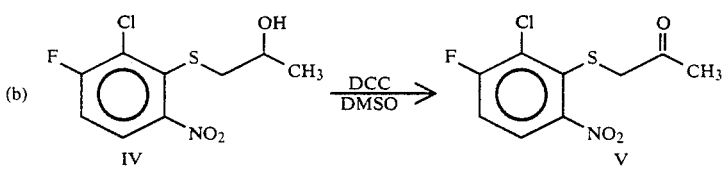

$^1$H—NMR (CDCl$_3$—TMS)δ1.2(3H,d,—CH—C$\underline{H}$$_3$)
2.78(2H, m.S—C$\underline{H}$$_2$)

3.51 (1H,m,N—C$\underline{H}$—CH$_3$)

3.83(1H,s,N—$\underline{H}$) 6.28(1H,dd,C$_5$$\underline{H}$) 6.55(1H,dd,C$_6$—$\underline{H}$).

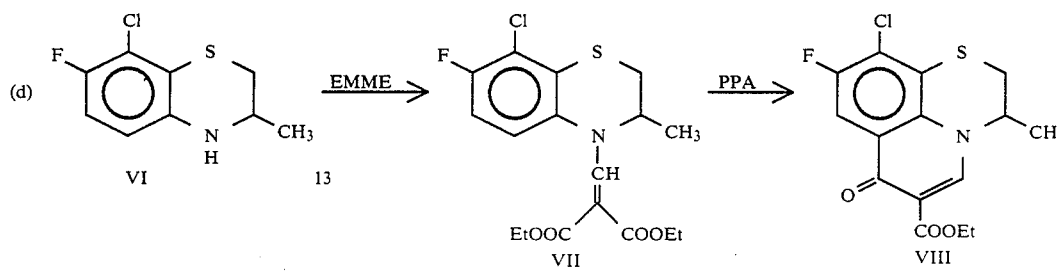

3.6 g (0.0165 mols) of benzothiazine (VI) and 3.57 g (0.0165 mols) of diethylethoxy-methylenmalonate (EMME) are kept under stirring and heated up to 160° C. for 8 hours, distilling off the alcohol as it is formed TLC 1/1 ethyl ether/petroleum ether).

At the end by cooling and diliuting with isopropyl ether, a withish solid (VII) precipitates, which is filtered (25 g). This product is added to 15 g polyphosphoric acid (PPA), previously heated to 60° C. and the mixture kept under stirring for 1 hour at 160° C.

The product is then poured in a water-ice mixture, and the cyclised derivative precipitates as a white solid. After filtration 1.9 g 10-chloro-9-fluoro-2,3-dihydro-3-methyl-7-oxo-7H pyrido [1,2,3 de][1.4] benzothiazine-6-ethyl carboxylate are obtained.

Yield 33.6%.
I.R. (nujol) 1.725 and 1.680 cm (νC=O).
$^1$H—NMR (CDCl$_3$—TMS)δ 1.45(3H,t,—CH$_2$—CH$_3$) 1.63(3H,d,N—CH—CH$_3$) 3.64 and 3.15(2H,dd,—S—C$\underline{H}$$_2$) 4.38(2H,q,$\overline{C}$$\underline{H}$$_2$CH$_3$)

4.7(1H,m,N—C$\underline{H}$—)

7.98(1H,s,C$_8$—$\underline{H}$) 8.4(1H,s,C$_5$—$\underline{H}$).

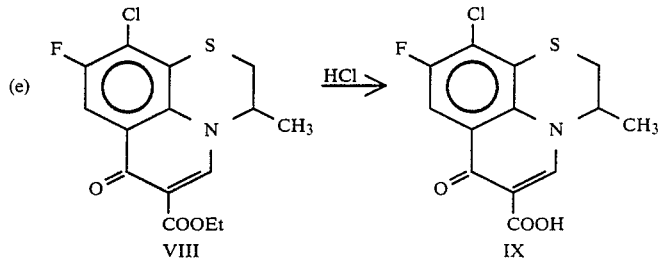

1.9 g ester (VIII) are suspended in 20 ml concentrated HCl and 40 ml water, the suspension is heated under reflux for 2 hours, then it is cooled, and the whitish solid which is formed is filtered off (1.58 g) 10 chloro-9-fluoro-2,3-dihydro-3-methyl-7-oxo-7H-pyrido [1,2,3 de][1,4] benzothiazine-6-carboxylic acid.
Yield 90.6%.
m.p.: >320° C.
IR(nujol) 3.360 cm$^{-1}$ (νO—H) 1.720 cm$^{-1}$ (νC=O).
$^1$H—NMR (CF$_3$COOH—TMS)δ 1.8(3H,d,—C$\underline{H}$$_3$) 3.39 and 3.78(2H,dd,—S—C$\underline{H}$$_2$)

5.42(1H,m,N—C$\underline{H}$—)

8.18(1H,d,C$_8$—$\underline{H}$) 9.46(1H,s,C$_5$—$\underline{H}$).

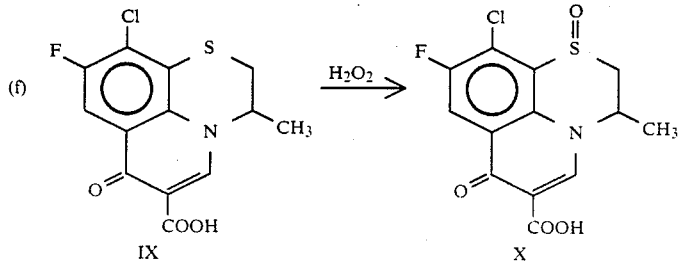

1.6 g of sulfide (IX) are suspended in 14 ml formic acid, then 0.6 ml 30% H$_2$O$_2$ are added. After keeping under stirring for 40', water is added and the precipitate is filtered and washed with ethanol. 1,04 g 10-chloro-9-fluoro-2,3-dihydro-3-methyl-7-oxo-7H-pyrido [1,2,3 de][1.4] benzothiazine-1-oxide-6-carboxylic acid is obtained.
Yield 61.8%.

$^1$H—NMR(CF$_3$COOH—TMS)$\delta$
1.8(3H,d,—C$\underline{H}_3$)3.26 and 3.45(2H,dd,—S—C$\underline{H}_2$)

5.15(1H,m,N—C$\underline{H}$—)

8.2(1H,d,C$_8$—$\underline{H}$) 9.1(1H,s,C$_5$—$\underline{H}$).

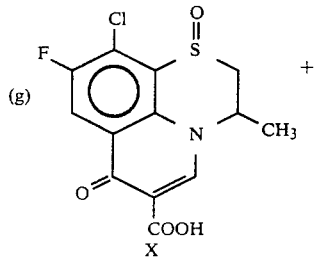

(g)

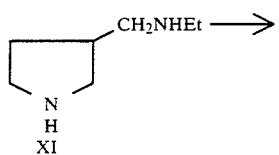

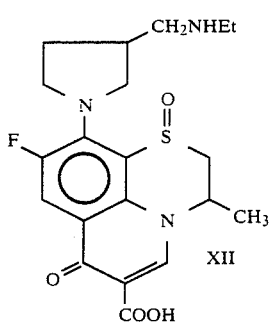

0.6 g (0.0018 mols) sulfoxide (X) are suspended in 20 ml DMF, 0.8 g (0.0062 mols) N-ethyl-3-pyrrolidinmethaneamine are added and the mixture is allowed to react for 1 hours at 70° C. The solution is cooled and the solvent evaporated; the residue taken up in EtOH gives 0.56 g 10[3-[(ethylamino)methyl]-1-pyrrolidinyl]-9-fluoro-2,3-dihydro-3-methyl-7-oxo-7H pyrido [1,2,3 de][1,4] benzothiazin-1-oxide carboxylic acid as a yellow solid.

Yield 73%.

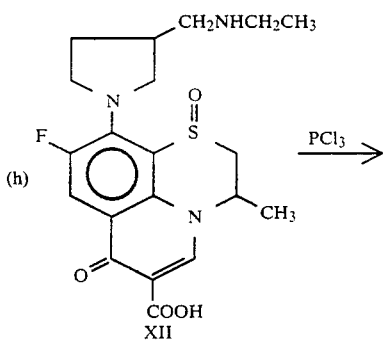

(h)

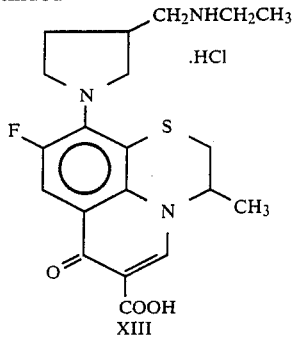

0.36 g (0.85 mmols) sulfoxide (XII) are suspended in 20 ml DMF, the solution is cooled to 0°–5° C. then 0.22 ml (2.53 mmols) PCl$_3$ are slowly added dropwise. After 15' reaction in the cold, 10 ml water are added to eliminate the PCl$_3$ excess, and the product is kept under stirring at room temperature for about 1 hours.

The solvent is evaporated, the residue is taken up in EtOH and the insoluble solid obtained with 61% yield is filtered off.

The 10-3-[(ethylamino)methyl]1-pyrrolidinyl]-9-fluoro-2,3-dihydro-3-methyl-7-oxo-7H-pyrido [1,2,3 de][1,4] benzothiazine-6-carboxylic acid hydrochloride thus obtained has the following characteristics:

m.p.: 257°–259° C.

UV (H$_2$O)$\lambda_{max}$ 247 and 301 nm.

$^1$H—NMR(CF$_3$COOH)$\delta$ 1.5(3H,m,CH$_2$C$\underline{H}_3$) 1.83(3H,m,N—CHC$\underline{H}_3$) 3.13-4.42(13H, m, —C$\underline{H}_2$—) 5.43(1H,m,H vicinal $\overline{S}$)

8.27(1H,d,C$_8$—H, J$_{H-F}$10.5

9.4(1h,s,C$_5$—$\underline{H}$).

Elemental analysis: Calculated: C=54.35%; H=5.70%; N=9.50%. Found: C=54.05%; H=5.78%; N=9.45%.

EXAMPLE 2

Preparation of:

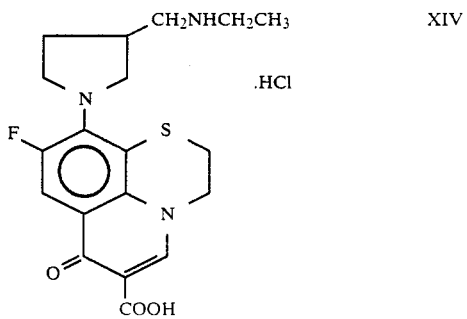

10-[3[(ethylamino)methyl]-1-pyrrolidinyl]-9-fluoro-2,3-dihydro-7-oxo-7H-pyrido [1,2,3 de][1,4] benzothiazine-6-carboxylic acid hydrochloride. (XIV) is prepared starting from 10-chloro-9-fluoro-2,3-dihydro-7-oxo-7H-pyrido [1,2,3 de][1,4] benzothiazine-1-oxide-6-carboxylic acid synthesized according to the method described in Italian Patent Application n. 19790 A/84 by nucleo philic substitution with N-ethyl-3-pyrrolidinmethane amine and successive reduction with PCl$_3$.

The method is identical with the one described in Example 1 and the product characteristics are as follows:

m.p.: 275°–277° C.
UV (H$_2$O)$\lambda_{max}$ 247 and 301 nm.
$^1$H—NMR(CF$_3$COOH—TMS)  δ
1.5(3H,t,CH$_2$C$\underline{H}_3$)3.1–4.4(13H,m,  —C$\underline{H}_2$)5.12 (2H,m,S—C$\underline{H}_2$)

8.2(1H,d,C$_8$—H, J$_{H—F}$10.5)

9.31(1H,s,C$_5$—$\underline{H}$).

Elemental Analysis: Calculated: C%=53.32; H%=5.42; N%=9.81. Found: C%=53.37; H%=5.38; N%=9.77.

EXAMPLE 3

Preparation of

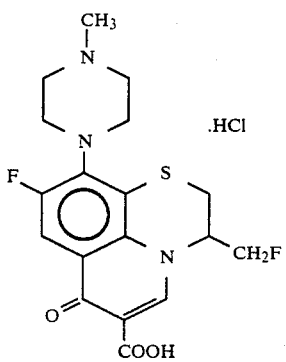

XXXIV 9-fluoro-3-fluoromethyl-10[4-(methyl)-1-piperazinyl]-2,3-dihydro-7-oxo-7H-pyrido[1,2,3 de][1.4] benzothiazine-6-carboxylic acid hydrochloride.

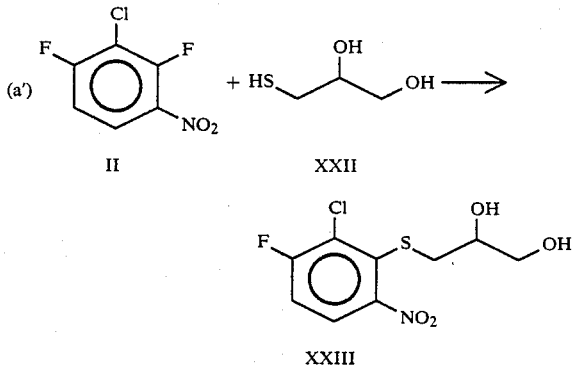

4.8 g (0.025 mols) 2,4-difluoro-3-chloronitro benzene (II) are dissolved in 30 ml dimethoxyethame, 3.6 ml (0.026 mols) triethylamine are added and keeping the temperature around −10° C., there are slowly added dropwise 2.1 ml (0.025 mols) of thioglycerin (XXII) dissolved in 10 ml dimethoxyethane. The mixture is kept for 1 hour at −10° C. and 6 hours at room temperature.

The solvent is evaporated, the residue in taken up in water and extracted with ethyl ether. After evaporating to dryness the crude product obtained is treated with isopropyl ether; a light yellow solid precipitates 4.9 g of 2(2,3-dihydroxythiopropyl)-3-chloro-4-fluoro-nitrobenzene (XXIII).

Yield 70%.

The product may be crystallized from CHCl$_3$.
m.p. 87°–88° C.
I.R. (nujol): 1.530 and 1.450 cm$^{-1}$ ($\nu$NO$_2$) 3.060 cm$^{-1}$ ($\nu$C—H) 3.200 cm$^{-1}$ ($\nu$O—H).
$^1$H—NMR (CDCl$_3$—TMS)δ 3.05(2H, d, —C$\underline{H}_2$—OH) 3.40–3.90(5H,m)

7.25(1H,dd,C$_5$—H J$_{H—F}$9 Hz) 7.6(1H,dd,C$_6$—$\underline{H}$ J$_{H—F}$6 Hz)

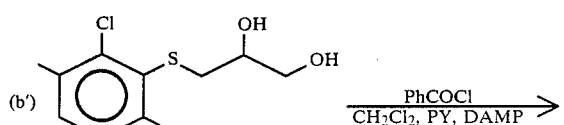

(XXIII)

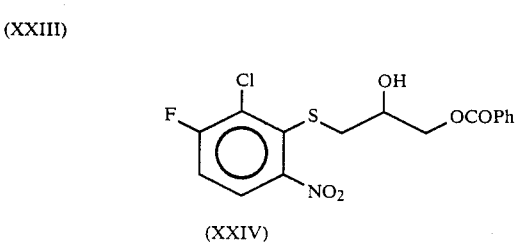

(XXIV)

28.1 g (0.1 mol) of diol (XXIII) are suspended in 150 ml CH$_2$Cl$_2$, 30 ml pyridine (the diol goes into solution) and 1.1 g (0.01 mol) dimethylaminopyridine are added, the solution is cooled to −40° C. and 12.6 ml (0.11 mols) benzoyl chloride dissolved in 150 ml CH$_2$Cl$_2$ are added dropwise very slowly. The reaction is continued for 3 hours at −30° C. and overnight at room temperature.

The reaction mixture is washed first with an acidic solution, then with a saturated NaHCO$_3$ solution and finally with water to neutral pH. The organic phase is made anhydrous and evaporated. 38 g of an oil are obtained which contains as impurity the starting compound. The crude is purified by column chromatography using as eluent petroleum ether/diethyl ether 1/1.

19.6 g of pure (XXIV) product are obtained. Yield 50%. m.p. 72°–73° C.

IR(nujol) 1530 and 1450 cm$^{-1}$ ($\nu$NO$_2$) 1700 cm$^{-1}$(C=O) 3080 cm$^{-1}$ ($\nu$C—H) 3460 cm$^{-1}$ ($\nu$OH).

$^1$H—NMR (CDCl$_3$—TMS) δ 3.1–3.3 (3H,m,S—C$\underline{H}_2$ and OH)

4.0–4.3 (1H,m,-C$\underline{H}$—OH)

4.4–4.5 (2H, d, C$\underline{H}_2$OCO) 7.2–8.1 (7H,m,aromatics).

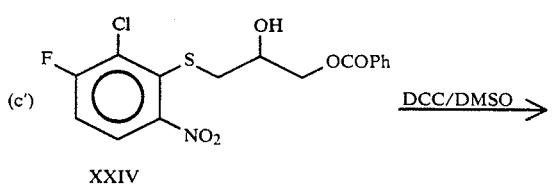

XXIV

-continued

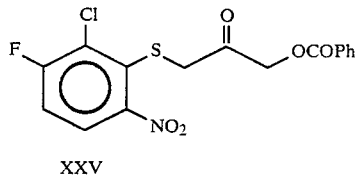
XXV

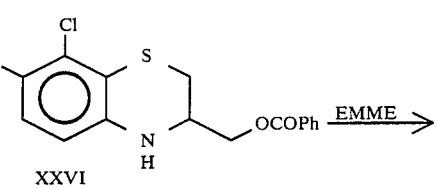
(e') XXVI 14 g (0.0363 mols) of (XXIV) and 14.23 g (0.069 mols) of dicyclohexylcarbodiimide are dissolved in 450 ml of anhydrous ethyl ether, 3.2 ml (0.045 mols) DMSO and 0.5 ml trifluoroacetic acid are added, the solution is kept at $-10°$ C. for 10', then at room temperature for 1 hour. 5 g (0.055 mols) oxalic acid dissolved in 20 ml methanol are then added, to destroy the excess of DCC. After about 30' the dicyclohexyl urea which is formed is filtered off and washed thoroughly with $CH_2Cl_2$.

The solution is evaporated and the residue treated with methanol. 10.8 g product (XXV) are obtained, free from dicyclohexylurea.

Yield 77%, m.p. 87°–88° C.

IR(nujol) 1450 and 1530 cm$^{-1}$ ($\nu NO_2$) 1725 cm$^{-1}$ ($\nu C=O$) 3080 cm$^{-1}$ (C—H)

$^1$H—NMR (CDCl$_3$—TMS) δ 3.8 (2H, s, S—C$\underline{H}_2$) 4.9 (2H,s, C$\underline{H}_2$OCO) 7.05–8.00 (7H,m,aromatics).

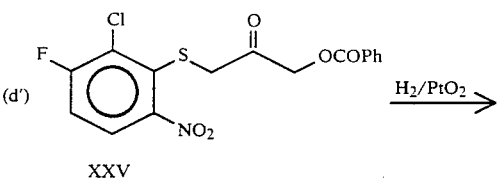
(d') XXV

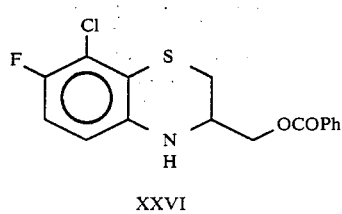
XXVI 9.6 g (0.025 mols) of product (XXV) abd 0.96 g (10% by wt.) of PtO$_2$ are suspended in 400 ml methanol and hydrogenating under normal pressure and at room temperature for about 16 hours is performed. The catalyst is then filtered off and the solvent is evaporated obtaining 8 g of a white-yellowish solid; the crude is taken up in diisopropyl ether and the obtained solid is filtered. 3.7 g of product (XXVI) are recovered. The ether solution is acidified with a saturated solution of p-toluensulfonic acid in Et$_2$O and the obtained precipitate is filtered. 2.3 g of thiazine p-toluensulfonate (XXVI) are obtained, with an overall yield of 61%.

m.p. 107°–108° C.

IR(nujol) 1710 cm$^{-1}$ ($\nu C=O$) 3380 cm$^{-1}$ ($\nu N$—H).

$^1$H—NMR (CDCl$_3$—TMS) δ 3.1 (2H, d, S—C$\underline{H}_2$) 4.0 (2H, m, N$\underline{H}$ and N—C$\underline{H}$) 4.25–4.60 (2H,m,C$\underline{H}_2$OCO) 6.2–6.4 (1$\underline{H}$, dd, C$_5$—$\underline{H}$) 6.55–6.80 (1H, t, C$_6$—$\underline{H}$) 7.3–8.1 (5H, m, aromatics)

m.p. 193° C.–194° C. (thiazine p-toluensulfonate)

XXVII 0.55 g (1.63 mmols) of product (XXVI) and 0.66 ml (3.26 mmols) diethylethoxymethylenmalonate are put in a 25 ml flask and heated at 170° C. distilling the ethanol that is forming.

After about 7 hrs reaction, until the starting product has disappeared (TLC petroleum ether/ethyl acetate 85/15), the glassy solid obtained is purified through flash-chromatography using the same eluents of the TLC.

0.566 g of product (XXVII) are obtained. Yield 68%. m.p. 97°–98° C.

IR(nujol) 1615 cm$^{-1}$ ($\nu C=O$ α, β unsaturated) 1715 cm$^{-1}$ ($\nu C=O$) 3060 cm$^{-1}$ ($\nu C$—H).

$^1$H—NMR (CDCl$_3$—TMS) δ 1.0–1.3 (6H,q,CH$_2$C$\underline{H}_3$) 3.1–3.6 (2H,m,S—C$\underline{H}_2$) 3.65–4.60

7.3–8.0 (6H,m,aromatics and $\overset{|}{C}=\overset{|}{C}\underline{H}$—N)

6.65–7.00 (2H,m,aromatics benzothiazine ring)

(7H,m,C$\underline{H}_2$CH$_3$ and C$\underline{H}_2$OCO and N—$\overset{|}{C}$H)

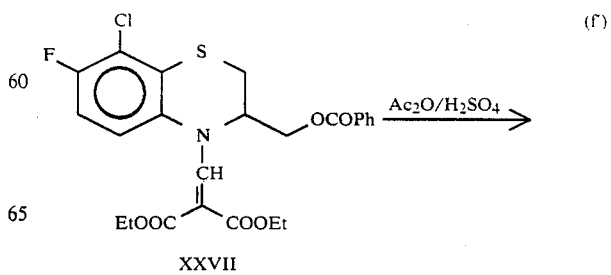
(f') XXVII

-continued

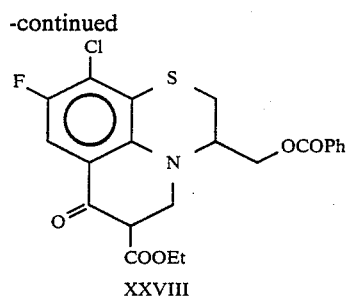
XXVIII

Keeping the temperature below 10° C., 2.5 ml sulphonic acid and 10 ml acetic anhydride are mixed, then the temperature is allowed to rise to room and 2.4 g of product (XXVII) are added. Heating to 70°–80° C. follows, until the reagent disappears (TLC petroleum ether/ethyl acetate 1/1), the solution is diluted with water and extracted with $CH_2Cl_2$. The organic phase, made anhydrous and evaporated, gives 2 g of product (XXVIII) as a white solid.

Yield 91% m.p. 210°–211° C.

IR(nujol) 1645 cm$^{-1}$ ($\nu$C=O keton) 1670 cm$^{-1}$ ($\nu$C=O ester $\alpha,\beta$-unsaturated) 1725 cm$^{-1}$ ($\nu$C=O esther) 3050 and 3090 cm$^{-1}$ ($\nu$C—H).

$^1$H—NMR (CF$_3$COOH—TMS) $\delta$ 1.1 (3H,t,CH$_2$CH$_3$) 3.35–3.70(2H,m,S—CH$_2$) 4.10–4.45 (2H,q,CH$_2$CH$_3$) 4.6–4.8 (2H,m,CH$_2$OCO)

5.3–5.6 (1H,m,N—CH)

7.0–8.0 (6H,m,aromatics) 9.0 (1H,s,C=CH—N).

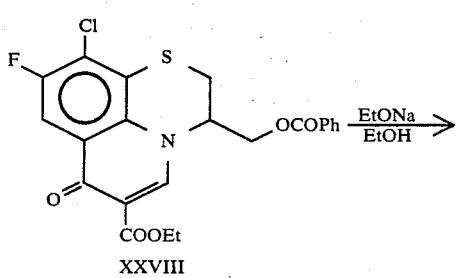
XXVIII

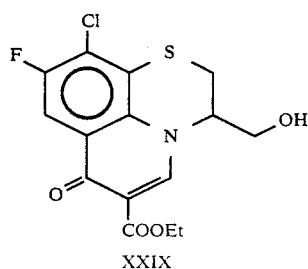
XXIX

Sodium ethylate is first prepared adding 0.112 g (4.86 mmols) sodium to 100 ml absolute ethanol in an anhydrous surrounding, then 2.04 g (4.42 mmols) (XXVIII) are added and the reaction is kept on until the reagent disappears (TLC AcOEt). The solution is concentrated, then diluted with water and extracted with $CH_2Cl_2$. The organic phase is made anhydrous and evaporated giving product (XXIX) with an impurities of ethyl benzoate. This can be eliminated by taking up the product in ethyl ether and filtering off the insolubles. 1.42 g are obtained.

Yield 90%. m.p. 247°–248° C.

IR(nujol) 1610 cm$^{-1}$ ($\nu$C=O keton) 1710 cm$^{-1}$ ($\nu$C=O ester) 3350 cm$^{-1}$ ($\nu$O—H).

$^1$H—NMR (CDCl$_3$—TMS) $\delta$ 1.4(3H,t,CH$_2$CH$_3$) 3.4–3.8(2H,m,s—CH$_2$) 3.9–4.4(2H,m,CH$_2$OH) 4.5 (2H,q,CH$_2$CH$_3$)

5.4(1H,m,—CH—N)

8.1 (1H,d,C$_8$—H) 9.4(1H,s,C$_5$—H).

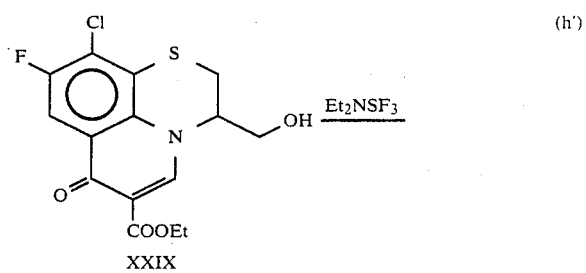
XXIX (h')

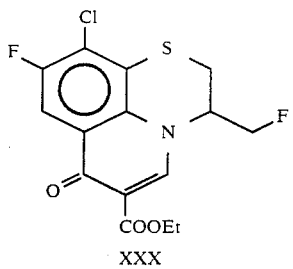
XXX 1.4 g (4 mmols) of (XXIX) are suspended in 150 ml $CH_2Cl_2$. 3 ml (2 mmols) of diethylaminosulphotrifluoride are added (everything goes into solution) and the reaction is left to proceed at room temperature following its course in TLC ($CH_2Cl_2$/MeOH 50/1). After about 20 hours, a saturated NaHCO$_3$ water solution is added very slowly to alkaline pH. The organic phase is separated and the product purified by flash chromatography using as eluent $CH_2Cl_2$/MeOH 90/1. 0.78 g of product (XXX) are recovered.

Yield 55%.

IR(nujol) 1020 cm$^{-1}$ ($\nu$C—F) 1650 cm$^{-1}$ ($\nu$C=O keton) 1680 cm$^{-1}$ ($\nu$C=O ester) 3050 and 3090 cm$^{-1}$ ($\nu$C—H).

$^1$H—NMR (CDCl$_3$—TMS) $\delta$ 1.4(3H,t,CH$_2$CH$_3$) 3.3–3.6 (2H,m,S—CH$_2$) 4.4 (2H,q,CH$_2$CH$_3$)

4.50–4.95 (3H,m,CH$_2$F and N—CH—CH$_2$F)

8.05 (1H,d,C$_8$—H) 8.4 (1H,s,C$_5$—H).

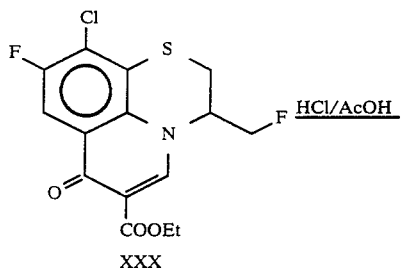

XXX

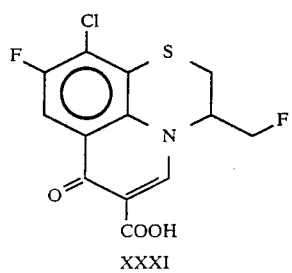

XXXI 0.78 g of (XXX) are suspended in 40 ml acetic acid and 80 ml 37% HCl and kept boiling until the starting product disappears (TLC CH₂Cl₂/MeOH 90/1). Most of the solvent is evaporated and the residue taken up in water; the obtained solid is filtered and washed well with water. 0.63 g of a white solid are obtained corresponding to product (XXXI).

Yield 87%. m.p. >300° C.

IR(nujol) 1040 cm⁻¹($\nu$C—F) 1610 cm⁻¹($\nu$C=O keton) 1745 cm⁻¹(C=O acid) 3080 cm⁻¹($\nu$C—H).

¹H—NMR (DMSO—TMS)δ 3.5–3.8 (2H, m, S—C$\underline{H}_2$) 4.50–5.05 (2H, m, C$\underline{H}_2$F)

5.4–5.7 (1H,m,N—C$\underline{H}$—CH₂F)

8.0 (1H, d, C₈—$\underline{H}$) 9.0 (1H, s, C₅—$\underline{H}$)

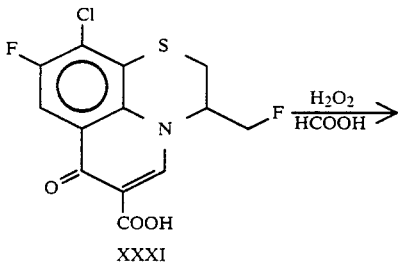

XXXI

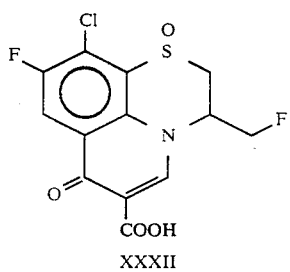

XXXII 0.5 g. (1.5 mmols) of (XXXI) are suspended in 5 ml. formic acid and 0.183 ml. (1.6 mmols) 30% H₂O₂ are added. The reaction is allowed to proceed at room temperature for 3 hrs checking in TLC (CH₂Cl₂/MeOH 50/1) the disappereance of the reagent.

After diluting with water and stirring for 1 h, the formed precipitate is filtered. 0.48 g. product (XXXII) are obtained as a white solid.

Yield 93%.

m.p. 248°–249° C.

IR(nujol) 1045 cm⁻¹($\nu$C—F) 1065 cm⁻¹($\nu$S=O) 1610 cm⁻¹($\nu$C=O keton) 1725 cm⁻¹($\nu$C=O acid) 3050 cm⁻¹($\nu$C—H).

¹H—NMR (DMSO—TMS) 3.65–4.20 (2H, m, S—C$\underline{H}_2$) 4.8–5.5 (2H, m, C$\underline{H}_2$F)

5.65–5.90 (1H,m,N—C$\underline{H}$—CH₂F)

8.5 (1H, d, C₈—$\underline{H}$) 9.0 (1H, s, C₅—$\underline{H}$).

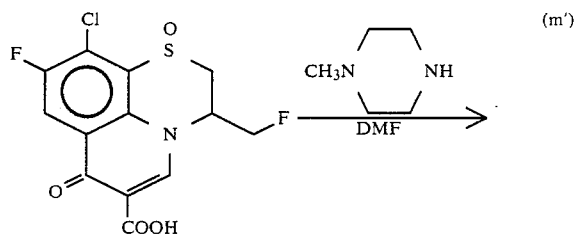

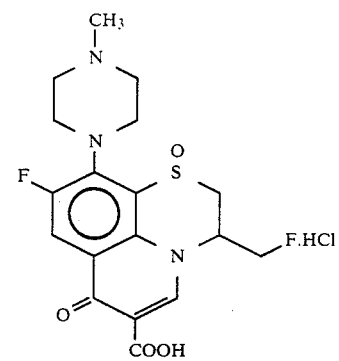

0.45 g. (1.3 mmols) (XXXII) are suspended in 10 ml. dimethylformamide, 1 ml. (9 mmols) of N-methylpiperazine are added, heating then for 1 h. at 100° C. The solvent is evaporated, and the residue is taken up in absolute ethanol. Keeping the solution in agitation for 30 minutes, a precipitate is obtained which is filtered off and washed with Et₂O.

0.1 g of product (XXXIII) is obtained. By partial evaporation of the solvent another 0.12 g are obtained.

Yield 38%.

IR(nujol) 1040 cm⁻¹ ($\nu$C—F and S=O) 1620 cm⁻¹ ($\nu$C=O keton) 1725 cm⁻¹ ($\nu$C=O acid).

¹H—NMR (DMSO—TMS) δ 2.5(3H,s,N—C$\underline{H}_3$) 3.0–3.9 (10H,m,s—C$\underline{H}_2$ and N—C$\underline{H}_2$) 4.75–5.30 (2H,m,C$\underline{H}_2$F)

5.6–5.8(1H,m,N—C$\underline{H}$—CH₂F)

8.30–8.45(1H,dd,C₈—$\underline{H}$) 8.95–9.05(1H,d,C₅—$\underline{H}$).

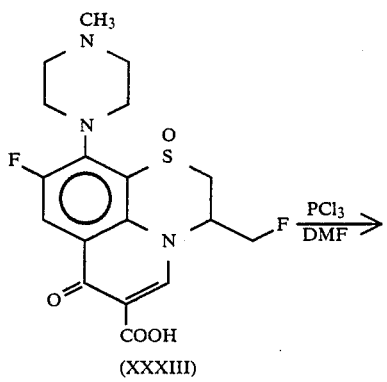

(XXXIII)

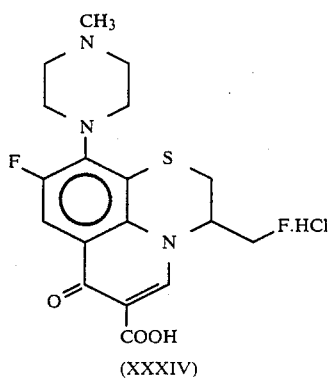

(XXXIV)

0.1 g (0.22 mmols) (XXXIII) are dissolved in 4 ml dimethylformamide; after cooling to 0° C., 0.1 ml (1.1 mmols) PCl₃ are added. The reaction is allowed to proceed for 30' at 0° C., then water is added and the solution is kept under stirring for 1 h at room temperature. The solvent is evaporated and the residue taken up in absolute ethanol. A white solid precipitates which is filtered off and washed well with EtOH.

60 mg product (XXXIV) are obtained.
Yield 57%.
m.p. 295°–298° C.
IR(nujol) 1025 cm$^{-1}$ ($\nu$C—F) 1620 cm$^{-1}$ ($\nu$C=O keton) 1720 cm$^{-1}$ ($\nu$C=O acid).
UV (H₂O)$\lambda_{max}$ 245 and 295 nm.
¹H—NMR (DMSO—TMS) δ 2.8(3H,s,N—C$\underline{H}_3$)3-.1–3.6(10H,m,S—C$\underline{H}_2$ and N—C$\underline{H}_2$)

4.7(1H,dt,C$\underline{H}_2$F J$_{H\text{-}F}$ 40Hz J$_{\widetilde{gem}}$ 9.7Hz J$_{\widetilde{vic}}$ 9.6Hz)

4.86(1H,dq,C$\underline{H}_2$F J$_{H\text{-}F}$ 40Hz J$_{\widetilde{gem}}$ 9.7Hz J$_{\widetilde{vic}}$ 5Hz)

5.5(1H,m,N—C$\underline{H}$—CH₂F) 7.86(1H,d,C₈—$\underline{H}$ J$_{H\text{-}F}$ 12Hz)

8.94 (1H,s,C₅—$\underline{H}$).

Elemental Analysis: Calculated: C%=50.06; H%=4.67; N%=9.73. Found: C%=50.10; H%=4.64; N%=9.70.

EXAMPLE 4

Preparation of

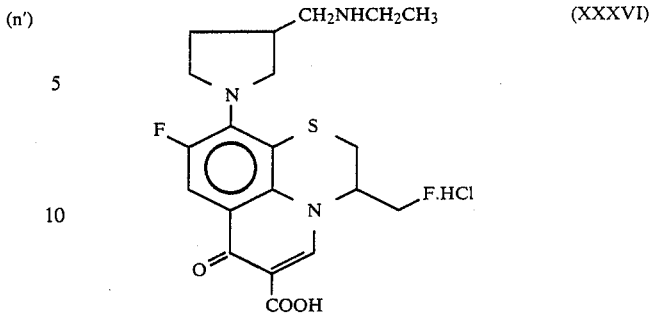

(XXXVI)

10-[3-[(ethylamino)methyl]-1-pyrrolidinyl]-9-fluoro-3-fluoromethyl-2,3-dihydro-7-oxo-7H-pyrido[1,2,3 de][1.4] benzothiazine-6-carboxylic acid hydrochloride.

Acid (XXXVI) is prepared starting from 10-Chloro-9-fluoro-3-fluoromethyl-2,3-dihydro-7-oxo-7H-pyrido [1,2,3 de][1.4] benzothiazine-1-oxide-6-carboxylic acid (XXXIII) described in Example 3, by nucleophilic substitution with N-ethyl-3-pyrrolidine-methanamine and successive reduction with PCl₃.

The method is identical with the one described in example 1 and the product as the following characteristics.

m.p. 232°–235° C.
UV (H₂O) $\lambda_{max}$ 245 and 299 nm.
Elemental Analysis: Calculated: E%=52.22; H%=5.26; N%=9.14. Found: C%=52.30; H%=5.24; N%=9.11.

"In vitro" antibacterial activity

The antibacterial activity of the compounds according to the present invention was evaluated against pathogenic strains of recent clinical isolation, both gram positive and gram negative.

Minimum inhibitory concentration (MIC) were determined by the diluition method in agar, using a multi-point inoculator (Denley Techn. Ltd. England). As a culture medium Mueller-Hinton agar (DIFCO) in Petri capsules was used.

The bacterial inoculum, originating from an overnight broth was inoculated by a multipoint and was standardized in such a way as to obtain 10⁵ colony forming units (CFU) per point.

After about 18 hrs incubation in a thermostat at 37° C., the bacterial growth was evaluated on each plate. MIC was defined as the lowest chemotherapeutic concentration still able to completely inhibit the bacterial growth, as evaluated by the absence of colony development on the inoculum point.

As reference standard compound 20, described in E.P. 0106489 was synthesized, which differs from the compound described in our example 1 only because it contains an oxygen atom (pyridobenzoxazine) instead of a sulfur atom (pyridobenzothiazine).

Table 1 shows the results relative to the compounds of examples 1 and 2 of the present invention and those relative to the reference standard.

These results show that the products of the present invention possess a wide and powerful activity spectrum on gram positive and gram negative strains.

TABLE 1

| | Minimum Inhibitory Concentrations (μg/ml) | | |
|---|---|---|---|
| Microorganism | Compound ex. 1 | Compound ex. 2 | E.P. 0106489 ex. 20 |
| Proteus 966 | 4 | 8 | 2 |
| Staphylococcus 7 | 0.12 | 1 | 0.25 |
| Staphylococcus 29 | 0.25 | 2 | 0.5 |
| E. coli 15 | 0.5 | 2 | 0.5 |
| E. coli 963 | 2 | 8 | 2 |
| Klebsiella 4 | 0.25 | 2 | 0.5 |
| Klebsiella 5 | 2 | 8 | 2 |
| Salmonella 9 | 0.5 | 4 | 1 |
| Salmonella 10 | 0.5 | 2 | 1 |
| Enterobacter 41 | 0.5 | 4 | 1 |
| Enterobacter 2653 | 0.25 | 1 | 0.25 |
| Citrobacter 118 | 2 | 8 | 4 |
| Proteus 25 | 4 | 8 | 1 |
| Citrobacter 120 | 4 | 8 | 2 |
| Staphylococcus 27 | 0.25 | 8 | 0.25 |
| Pseudomonas 19 | 32 | 128 | 64 |
| Pseudomonas 2437 | 64 | >128 | 128 |

We claim:

1. Pyrido-benzothiazine derivatives possessing high antibacterial activity and tissue bio-availability, having the following general formula:

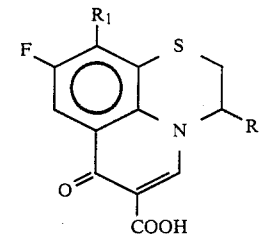

in which R is H or —CH₃ or —CH₂F and R₁ is N-alkyl-3-pyrrolidynalkylamine with $C_1$ to $C_6$ alkyls or if R is —CH₂F R₁ is

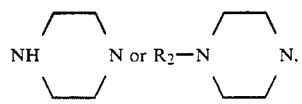

where $R_2$ is a $C_1$-$C_6$ alkyl or a $C_2$-$C_6$ alkenyl or an arylalkyl, possibly substituted by halogen, hydroxy or keto groups, both in the racemic form and in the optically active form.

2. Antibacterially active pharmaceutical compositions comprising as an active principle at least one of the pyrido-benzothiazine derivatives of general formula (I) of claim 1 and a pharmaceutically acceptable carrier.

* * * * *